US006935991B1

(12) United States Patent
Mangino

(10) Patent No.: US 6,935,991 B1
(45) Date of Patent: Aug. 30, 2005

(54) MEANS AND METHOD OF EXERCISING FEET AND LEGS OF BEDRIDDEN PATIENT

(76) Inventor: Denise F. Mangino, 651 Elder Ave., Apt. 3A, Phillipsburg, NJ (US) 08865

( * ) Notice: Subject to any disclaimer, the term of this patent is extended or adjusted under 35 U.S.C. 154(b) by 0 days.

(21) Appl. No.: 10/839,866

(22) Filed: May 7, 2004

(51) Int. Cl.[7] .......................... A63B 21/00; A61F 5/14; A61H 5/00

(52) U.S. Cl. ............................ 482/51; 482/79; 36/140; 601/27; 606/237

(58) Field of Search .............................. 482/51, 79–80, 482/148, 91; 280/816; 36/140; 606/237; 601/22, 27, 29–32; 602/28–29

(56) References Cited

U.S. PATENT DOCUMENTS

| | | | | |
|---|---|---|---|---|
| 1,509,793 A * | 9/1924 | Thompson | 482/79 |
| 1,996,614 A * | 4/1935 | Davis | 606/237 |
| 2,282,307 A * | 5/1942 | Davis | 606/237 |
| 2,700,832 A * | 2/1955 | Slovinski | 36/140 |
| 3,582,067 A * | 6/1971 | Rucks | 280/816 |
| 3,713,437 A * | 1/1973 | Wiedmer | 601/27 |
| D226,875 S | 5/1973 | Haworth, Jr. et al. | |
| 3,802,700 A * | 4/1974 | Mayo | 482/79 |
| 3,910,571 A | 10/1975 | Stenn | |
| 4,185,622 A * | 1/1980 | Swenson | 601/27 |
| 4,186,920 A * | 2/1980 | Fiore et al. | 482/79 |
| 4,390,177 A | 6/1983 | Biran et al. | |
| 4,925,184 A | 5/1990 | McJunkin, Jr. et al. | |
| 5,038,761 A * | 8/1991 | Richardson | 602/28 |
| 5,148,800 A * | 9/1992 | Pecheux | 601/29 |
| 5,176,130 A | 1/1993 | Kim | |
| 5,913,838 A | 6/1999 | Reilly | |
| 6,283,897 B1 * | 9/2001 | Patton | 482/79 |
| 6,589,141 B1 * | 7/2003 | Flaggs | 482/79 |

* cited by examiner

*Primary Examiner*—Stephen R. Crow
(74) *Attorney, Agent, or Firm*—Donald R. Schoonover

(57) ABSTRACT

The legs of a bedridden patient can be exercised by attaching a shoe-attachable unit to each shoe of the patient and rotating and maneuvering the legs of the patient via the shoe-attachable units.

3 Claims, 1 Drawing Sheet

MEANS AND METHOD OF EXERCISING FEET AND LEGS OF BEDRIDDEN PATIENT

BACKGROUND OF THE INVENTION

1. Field of the Invention

The present invention relates to the general art of medical devices and methods, and to the particular field of therapy.

2. Discussion of the Related Art

Many people find themselves bedridden for great lengths of time. In some cases, the person's muscles may atrophy. This can be the case with a person's legs and feet. For this reason, many health care facilities have therapists who help bedridden patients exercise while the patient remains in bed. The therapist helps the patient exercise certain muscles in a manner that ameliorates the effects of a long period of bed confinement.

Heretofore, a therapist was required to exercise each leg separately from the other leg. This is not efficient use of the therapist's time.

Therefore, there is a need for a means and a method for exercising a bedridden patient's feet that is efficient.

Therefore, there is a need for a means and a method for exercising a bedridden patient's legs that is efficient and will permit the exercise to be carried out while the patient is wearing shoes or lightweight sneakers.

Since most patient's feet will be different from the feet of other patients, any means and method used to conduct therapy that will permit the patient to retain his or her shoes in place must be amenable to accommodating different size shoes. This accommodation should not require a great deal of effort from the therapist, otherwise the purpose of the device to achieve efficiency may be vitiated.

Therefore, there is a need for a means and a method for exercising a bedridden patient's legs that is efficient and will permit the exercise to be carried out while the patient is wearing shoes and will efficiently accommodate shoes of varying sizes.

A therapist may wish to use one of his or her hands to help a patient or to steady himself or herself during the exercise. However, if both hands are required to manipulate an exercise device, this objective may be difficult to attain.

Therefore, there is a need for a therapy device that can make exercising a bedridden patient's leg more efficient while allowing a therapist to keep one hand free or exercise both legs at the same time.

Since all patients are slightly different and have different needs and comfort levels, a single device will not be efficient for use with all patients. Thus, it will be advantageous if a therapy device can be modified to meet the particular needs of an individual patient.

Therefore, there is a need for a therapy device that can make exercising a bedridden patient's foot more efficient and which can be customized to meet the needs of a particular patient.

PRINCIPAL OBJECTS OF THE INVENTION

It is a main object of the present invention to provide a means and a method for exercising a bedridden patient's leg that is efficient.

It is another object of the present invention to provide a means and a method for exercising a bedridden patient's leg that is efficient and will permit the exercise to be carried out while the patient is wearing shoes.

It is another object of the present invention to provide a means and a method for exercising a bedridden patient's feet that is efficient and will permit the exercise to be carried out while the patient is wearing shoes and will efficiently accommodate shoes of varying sizes.

It is another object of the present invention to provide a therapy device that can make exercising a bedridden patient's foot more efficient while allowing a therapist to keep one hand free.

It is another object of the present invention to provide a therapy device that can make exercising a bedridden patient's foot more efficient and which can be customized to meet the needs of a particular patient.

SUMMARY OF THE INVENTION

These, and other, objects are achieved by a means and a method of exercising the legs of a bedridden patient. The means includes a shoe-attachable unit that includes means for adjusting the size of the unit to accommodate shoes of various sizes. The unit further includes straps for attaching the unit to the patient's shoe, and a handle to be grasped by the therapist. The method is carried out by the therapist grasping the handle and manipulating the patient's foot via the shoe-attachable unit.

In an application of the present invention, the patient is usually bedridden, so it is not necessary to steady him or her. The present invention allows one hand per each leg, so that makes it possible to work both legs simultaneously. The therapist can grasp two units at the same time so both of a patient's legs can be exercised at the same time.

Using the means and method embodying the present invention will permit a therapist to exercise both legs of a patient at the same time while the patient wears his or her shoes. The means and method is easily and quickly adjusted to accommodate various shoe sizes. The therapy device can be customized to meet the particular needs of a patient and can be used in a manner that frees one hand of the therapist for other tasks. The means and method of the present invention is thus both efficient and preferable to most patients and therapists.

BRIEF DESCRIPTION OF THE DRAWING FIGURES

DETAILED DESCRIPTION OF THE PREFERRED EMBODIMENT

Figure 3:
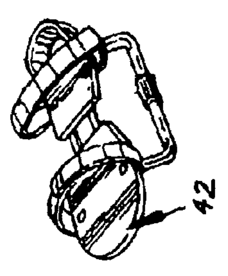
FIG. 3 is a further reduced perspective view of the device shown in FIG. 1 in a use condition.
Figure 2:
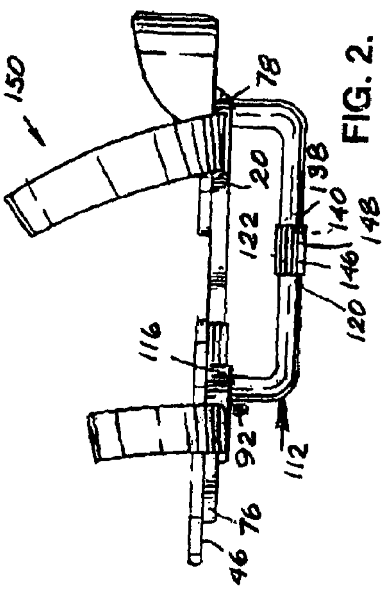
FIG. 2 is a reduced side elevational view of the device shown in FIG. 1.
Figure 1:
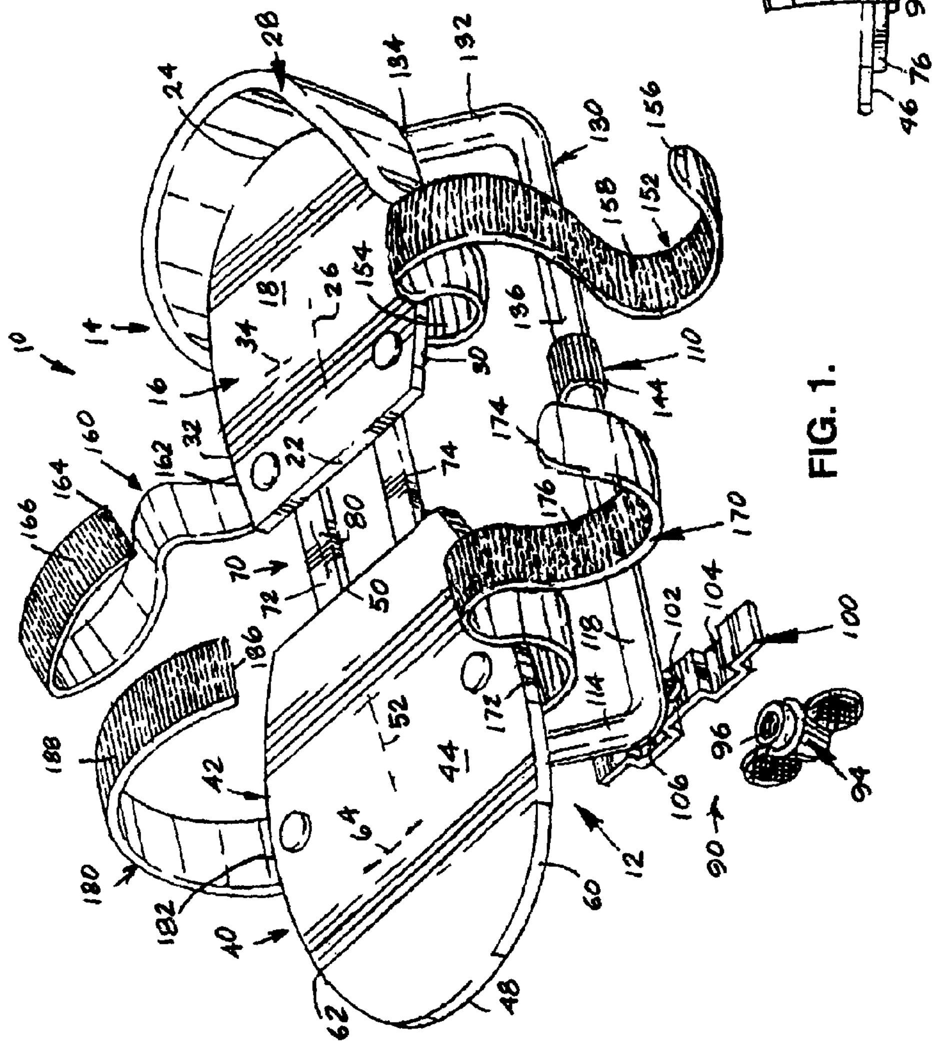
FIG. 1 is a perspective view of a device for performing foot therapy embodying the present invention.

Other objects, features and advantages of the invention will become apparent from a consideration of the following detailed description and the accompanying drawings.

Referring to the Figures, it can be understood that the present invention is embodied in a device 10 for performing leg therapy. Device 10 comprises a base unit 12 that is adapted to be secured to a shoe of a patient for use. Base unit 12 includes a heel section 14 which includes a base plate 16 which has a first surface 18 that is a top surface when the base unit 12 is secured to a shoe and which is adapted to abut a sole of a shoe of a patient adjacent to the heel of the shoe when the base unit 12 is secured to the shoe of the patient. Plate 16 further includes a second surface 20 which is a bottom surface when the base unit 12 is secured to a shoe, a first end 22 which is a forward end when the base unit 12 is secured to a shoe, a second end 24 which is a rear end when the base unit 12 is secured to a shoe, and a longitudinal axis 26 which extends between the first end 22 of the base plate 16 and the second end 24 of the base plate 16. A heel ridge 28 is secured to the second end 24 of the base plate 16 and is oriented at a right angle to the first surface 18 of the base plate 16 and which is adapted to engage the heel of the shoe of the patient when the base unit 12 is secured to the shoe of the patient. The shape of the heel ridge 28 is arcuate. The heel section 14 further includes a first side 30, a second side 32, and a transverse axis 34 which extends between the first side 30 of the heel section 14 and the second side 32 of the heel section 14.

Base unit 12 further includes a forward section 40 which includes a base plate 42 which has a first surface 44 that is a top surface when the base unit 12 is secured to a shoe and which is adapted to abut a sole of a shoe adjacent to a toe of the shoe of a patient when the base unit 12 is secured to the shoe of the patient. Forward section 40 further includes a second surface 46 which is a bottom surface when the base unit 12 is secured to a shoe. Forward section 40 further includes a first end 48 which is a forward end when the base unit 12 is secured to a shoe, a second end 50 which is a rear end when the base unit 12 is secured to a shoe, and a longitudinal axis 52 which extends between the first end 48 of the base plate 42 of the forward section 40 and the second end 50 of the base plate 42 of the forward section 40 and which is co-linear with the longitudinal axis 26 of the heel section 14 of the base unit 12. The forward section 40 further includes a first side 60, a second side 62, and a transverse axis 64 extending between the first side 60 of the forward section 40 and the second side 62 of the forward section 40.

Device 10 further includes a size-adjusting unit 70 movably connecting the forward section 40 to the heel section 14 and which includes two rods 72 and 74. Each rod 72, 74 includes a first end 76 movably attached to the second surface 46 of the forward section 40 and a second end 78 movably attached to the second surface 20 of the heel section 14. Each rod 72, 74 has a longitudinal axis, such as longitudinal axis 80 of rod 72, which extends between the first end 76 of each rod 72, 74 and the second end 78 of each rod 72, 74 and which extends in the direction of the longitudinal axis 52 of the forward section 40. The two rods 72, 74 are spaced apart from each other in the direction of the transverse axis 34 of the heel section 14.

A bracket unit 90 includes an externally threaded bolt 92 mounted in the forward section 40 and extending from the second surface 46 of the forward section 40, a wing nut 94 having a threaded section 96 that is adapted to threadably engage the threaded bolt 92, and a bracket element 100 which includes a central hole 102 adapted to accommodate the threaded bolt 92. Bracket element 100 further includes two channels 104 and 106. Each channel 104, 106 is sized to snugly accommodate one of the two rods 72, 74 of the size-adjusting unit 70.

Device 10 further includes an adjustable handle unit 110 which includes a first L-shaped section 112 which has a first portion 114 with a proximal end 116 thereof fixedly mounted on the second surface 46 of the forward section 40 and a second portion 118 which extends in the direction of the longitudinal axis 52 of the forward section 40 toward the second end 50 of the forward section 40. The second portion 118 of the first L-shaped section 112 has a distal end 120 which is spaced apart from the second end 50 of the forward section 40 and which is also spaced apart from the second surface 46 of the forward section 40. The second portion 118 of the first L-shaped section 112 has a screw thread 122 defined thereon adjacent to the distal end 120 of the second portion 118 of the first L-shaped section 112.

A second L-shaped section 130 has a first portion 132 with a proximal end 134 thereof fixedly mounted on the second surface 20 of the heel section 14 and a second portion 136 which extends in the direction of the longitudinal axis 26 of the heel section 14 toward the first end 22 of the heel section 14. The second portion 136 of the second L-shaped section 130 has a distal end 138 which is spaced apart from the first end 22 of the heel section 14 and which is also spaced apart from the second surface 20 of the heel section 14. The second portion 136 of the second L-shaped section 130 has a screw thread 140 defined thereon adjacent to the distal end 138 of the second portion 136 of the second L-shaped section 130.

A double threaded nut 144 has a first threaded portion 146 that is adapted to threadably engage the screw thread 122 defined on the second portion 118 of the first L-shaped section 112 and a second threaded portion 148 that is adapted to threadably engage the screw thread 140 defined on the second portion 136 of the second L-shaped section 130.

A strap unit 150 includes a first strap 152 which includes a proximal end 154 fixedly attached to the heel section 14 adjacent to the first side 30 of the heel section 14 and adjacent to the first end 22 of the heel section 14. The first strap 152 includes a distal end 156 and hook-and-loop fastener material 158 thereon.

A second strap 160 includes a proximal end 162 fixedly attached to the heel section 14 adjacent to the second side 32 of the heel section 14 and adjacent to the first end 22 of the heel section 14. The second strap 160 further includes a distal end 164 and hook-and-loop fastener material 166.

A third strap 170 includes a proximal end 172 fixedly attached to the forward section 40 adjacent to the first side 60 of the forward section 40 and adjacent to the first end 48 of the forward section 40. The third strap 170 includes a distal end 174 and hook-and-loop fastener material 176 thereon.

A fourth strap 180 includes a proximal end 182 fixedly attached to the forward section 40 adjacent to the second side 62 of the forward section 40 and adjacent to the first end 48 of the forward section 40. The fourth strap 180 includes a distal end 186 and hook-and-loop fastener material 188 thereon.

The method of using device 10 will now be described. A first device 10 is fitted to and secured to one shoe of the patient using the size-adjusting features described above and the strap unit 150 described above. The therapist then grasps the adjustable handle unit 110 of the first device 10 and rotates and maneuvers the first device 10 and the leg connected to the foot of the patient that is attached to the first shoe using the adjustable handle unit 110.

The therapist can also exercise the patient's other foot by fitting and securing a second device 10 to the second shoe of the patient, grasping the adjustable handle 110 unit of the second device 10 and rotating and maneuvering the second leg connected to the foot of the patient using the second device 10 while simultaneously rotating and maneuvering the first leg connected to the first foot of the patient using the first device 10. Alternatively, if only one device 10 is used, the therapist will have one hand free to complete other tasks if desired.

It is understood that while certain forms of the present invention have been illustrated and described herein, it is not to be limited to the specific forms or arrangements of parts described and shown.

What is claimed and desired to be secured by Letters Patent is as follows:

1. A device for performing foot leg therapy comprising:

a) a base unit that is adapted to be secured to a shoe of a patient for use, said base unit including (1) a heel section which includes a base plate which has a first surface that is a top surface when said base unit is secured to a shoe and which is adapted to abut a sole of a shoe of a patient adjacent to the heel of the shoe when said base unit is secured to the shoe of the patient, a second surface which is a bottom surface when said base unit is secured to a shoe, a first end which is a forward end when said base unit is secured to a shoe, a second end which is a rear end when said base unit is secured to a shoe, a longitudinal axis which extends between the first end of the base plate and the second end of the base plate, a heel ridge which is secured to the second end of the base plate and which is oriented at a right angle to the first surface of the base plate and which is adapted to engage the heel of the shoe of the patient when said base unit is secured to the shoe of the patient, the heel ridge being arcuate, the heel section further including a first side, a second side and a transverse axis extending between the first side of the heel section and the second side of the heel section;

(2) a forward section which includes a base plate which has a first surface that is a top surface when said base unit is secured to a shoe and which is adapted to abut a sole of a shoe adjacent to a toe of the shoe of a patient when said base unit is secured to the shoe of the patient, a second surface which is a bottom surface when said base unit is secured to a shoe, a first end which is a forward end when said base unit is secured to a shoe, a second end which is a rear end when said base unit is secured to a shoe, a longitudinal axis which extends between the first end of the base plate of the forward section and the second end of the base plate of the forward section and which is co-linear with the longitudinal axis of the heel section of said base unit, the forward section further including a first side, a second side and a transverse axis extending between the first side of the forward section and the second side of the forward section;

b) a size-adjusting unit movably connecting the forward section to the heel section and which includes (1) two rods, each rod including a first end movably attached to the second surface of the forward section and a second end movably attached to the second surface of the heel section, each rod having a longitudinal axis which extends between the first end of each rod and the second end of each rod and which extends in the direction of the longitudinal axis of the forward section, the two rods being spaced apart from each other in the direction of the transverse axis of the heel section, and (2) a bracket unit which includes (A) an externally threaded bolt mounted in the forward section and extending from the second surface of the forward section, (B) a wing nut having a threaded section that is adapted to threadably engage the threaded bolt, (C) a bracket element which includes a central hole adapted to accommodate the threaded bolt, and two channels, with each channel being sized to snugly accommodate one of the two rods of said size-adjusting unit, c) an adjustable handle unit which includes (1) a first L-shaped section having a first portion with a proximal end thereof fixedly mounted on the second surface of the forward section and a second portion which extends in the direction of the longitudinal axis of the forward section toward the second end of the forward section, the second portion of the first L-shaped section having a distal end which is spaced apart from the second end of the forward section and which is also spaced apart from the second surface of the forward section, the second portion of the first L-shaped section having a screw thread defined thereon adjacent to the distal end of the second portion of the first L-shaped section, (2) a second L-shaped section having a first portion with a proximal end thereof fixedly mounted on the second surface of the heel section and a second portion which extends in the direction of the longitudinal axis of the heel section toward the first end of the heel section, the second portion of the second L-shaped section having a distal end which is spaced apart from the first end of the heel section and which is also spaced apart from the second surface of the heel section, the second portion of the second L-shaped section having a screw thread defined thereon adjacent to the distal end of the second portion of the second L-shaped section, and (3) a double threaded nut which has a first threaded portion that is adapted to threadably engage the screw thread defined on the second portion of the first L-shaped section, and a second threaded portion that is adapted to threadably engage the screw thread defined on the second portion of the second L-shaped section, and d) a strap unit which includes (1) a first strap which includes a proximal end fixedly attached to the heel section adjacent to the first side of the heel section and adjacent to the first end of the heel section, the first strap including a distal end and hook-and-loop fastener material thereon, (2) a second strap which includes a proximal end fixedly attached to the heel section adjacent to the second side of the heel section and adjacent to the first end of the heel section, the second strap including a distal end and hook-and-loop fastener material thereon, (3) a third strap which includes a proximal end fixedly attached to the forward section adjacent to the first side of the forward section and adjacent to the first end of the forward section, the third strap including a distal end and hook-and-loop fastener material thereon, and (4) a fourth strap which includes a proximal end fixedly attached to the forward section adjacent to the second side of the forward section and adjacent to the first end of the forward section, the fourth strap including a distal end and hook-and-loop fastener material thereon.

2. A method for performing leg therapy comprising:

a) providing a first device for performing leg therapy which includes a base unit that is adapted to be secured to a shoe of a patient for use, said base unit including (1) a heel section includes a base plate which has a first surface that is a top surface when said base unit is secured to a shoe and which is adapted to abut a sole of a shoe of a patient adjacent to the heel of the shoe when said base unit is secured to the shoe of the patient, a second surface which is a bottom surface when said base unit is secured to a shoe, a first end which is a forward end when said base unit is secured to a shoe, a second end which is a rear end when said base unit is secured to a shoe, a longitudinal axis which extends between the first end of the base plate and the second end of the base plate, a heel ridge which is secured to the second end of the base plate and which is oriented at a right angle to the first surface of the base plate and which is adapted to engage the heel of the shoe of the patient when said base unit is secured to the shoe of the patient, the heel ridge being arcuate, the heel section further including a first side, a second side and a transverse axis extending between the first side of the heel section and the second side of the heel section;

(2) a forward section which includes a base plate which has a first surface that is a top surface when said base unit is secured to a shoe and which is adapted to abut a sole of a shoe adjacent to a toe of the shoe of a patient when said base unit is secured to the shoe of the patient, a second surface which is a bottom surface when said base unit is secured to a shoe, a first end which is a forward end when said base unit is secured to a shoe, a second end which is a rear end when said base unit is secured to a shoe, a longitudinal axis which extends between the first end of the base plate of the forward section and the second end of the base plate of the forward section and which is co-linear with the longitudinal axis of the heel section of said base unit, the forward section further including a first side, a second side and a transverse axis extending between the first side of the forward section and the second side of the forward section; a size adjusting unit movably connecting the forward section to the heel section and which includes;

(3) two rods, each rod including a first end movably attached to the second surface of the forward section and a second end movably attached to the second surface of the heel section, each rod having a longitudinal axis which extends between the first end of each rod and the second end of each rod and which extends in the direction of the longitudinal axis of the forward section, the two rods being spaced apart from each other in the direction of the transverse axis of the heel section; and (4) a bracket unit which includes;

(A) an externally threaded bolt mounted in the forward section and extending from the second surface of the forward section, (B) a wing nut having a threaded section that is adapted to threadably engage the threaded bolt, (C) a bracket element which includes a central hole adapted to accommodate the threaded bolt, and two channels, with each channel being sized to snugly accommodate one of the two rods of said size adjusting unit; an adjustable handle unit which includes, (1) a first L-shaped section having a first portion with a proximal end thereof fixedly mounted on the second surface of the forward section and a second portion which extends in the direction of the longitudinal axis of the forward section toward the second end of the forward section, the second portion of the first L-shaped section having a distal end which is spaced apart from the second end of the forward section and which is also spaced apart from the second surface of the forward section, the second portion of the first L-shaped section having a screw thread defined thereon adjacent to the distal end of the second portion of the first L-shaped section, (2) a second L-shaped section having a first portion with a proximal end thereof fixedly mounted on the second surface of the heel section and a second portion which extends in the direction of the longitudinal axis of the heel section toward the first end of the heel section, the second portion of the second L-shaped section having a distal end which is spaced apart from the first end of the heel section and which is also spaced apart from the second surface of the heel section, the second portion of the second L-shaped section having a screw thread defined thereon adjacent to the distal end of the second portion of the second L-shaped section, and (3) a double threaded nut which has a first threaded portion that is adapted to threadably engage the screw thread defined on the second portion of the first L-shaped section, and a second threaded portion that is adapted to threadably engage the screw thread defined on the second portion of the second L-shaped section; and a strap unit which includes, (1) a first strap which includes a proximal end fixedly attached to the heel section adjacent to the first side of the heel section and adjacent to the first end of the heel section, the first strap including a distal end and hook-and-loop fastener material thereon, (2) a second strap which includes a proximal end fixedly attached to the heel section adjacent to the second side of the heel section and adjacent to the first end of the heel section, the second strap including a distal end and hook-and-loop fastener material thereon, (3) a third strap which includes a proximal end fixedly attached to the forward section adjacent to the first side of the forward section and adjacent to the first end of the forward section, the third strap including a distal end and hook-and-loop fastener material thereon, and (4) a fourth strap which includes a proximal end fixedly attached to the forward section adjacent to the second side of the forward section and adjacent to the first end of the forward section, the fourth strap including a distal end and hook-and-loop fastener material thereon, b) fitting the first device onto a first shoe of the patient;

c) securing the first device to the first shoe of the patient;

d) grasping the adjustable handle unit of the first device;

e) rotating and maneuvering the first device and the leg connected to the foot of the patient attached to the first shoe using the adjustable handle unit.

3. The method as described in claim 2 further including providing a second device for performing foot and/or leg therapy; fitting the second device to a second shoe of the patient; securing the second device to the second shoe of the patient; grasping the adjustable handle unit of the second device while simultaneously grasping the adjustable handle unit of the first device; and rotating and maneuvering the second leg connected to the second foot of the patient using the second device while simultaneously rotating and maneuvering the first leg connected to the first foot of the patient using the first device.

* * * * *